US012527789B2

(12) United States Patent
Lorico et al.

(10) Patent No.: US 12,527,789 B2
(45) **Date of Patent: *Jan. 20, 2026**

(54) INHIBITION OF A TRIPARTITE VOR PROTEIN COMPLEX IN MULTICELLULAR ORGANISMS

(71) Applicants: Aurelio Lorico, Las Vegas, NV (US); Denis Corbeil, Dresden (DE); Mark F. Santos, Las Vegas, NV (US); Germana Rappa, Las Vegas, NV (US)

(72) Inventors: Aurelio Lorico, Las Vegas, NV (US); Denis Corbeil, Dresden (DE); Mark F. Santos, Las Vegas, NV (US); Germana Rappa, Las Vegas, NV (US)

(73) Assignees: Aurelio Lorico, Las Vegas, NV (US); Mark Santo, Las Vegas, NV (US); Germana Rappa, Las Vegas, NV (US); Patrizia Diana, Palermo (IT); TECHNISCHE UNIVERSITÄT DRESDEN, Dresden (DE); BASCK INVEST LIMITED, Cambridge (GB); Giuseppe Pizzorno, TN (US); Andrea Dagnino, Madrid (ES); Ottavio Dagnino, Palermo (IT); Baldesare Renda, Palermo (IT); Gaspare Spedale, Palermo (IT)

( * ) Notice: Subject to any disclaimer, the term of this patent is extended or adjusted under 35 U.S.C. 154(b) by 1374 days.

This patent is subject to a terminal disclaimer.

(21) Appl. No.: 17/255,715

(22) PCT Filed: Jun. 27, 2019

(86) PCT No.: PCT/IB2019/055462

§ 371 (c)(1),
(2) Date: Dec. 23, 2020

(87) PCT Pub. No.: WO2020/003204

PCT Pub. Date: Jan. 2, 2020

(65) Prior Publication Data

US 2021/0353616 A1 Nov. 18, 2021

Related U.S. Application Data

(60) Provisional application No. 62/690,616, filed on Jun. 27, 2018.

(30) Foreign Application Priority Data

Jun. 27, 2018 (GB) .................................... 1810556

(51) Int. Cl.

| | |
|---|---|
| ***A61K 31/496*** | (2006.01) |
| ***A61P 31/18*** | (2006.01) |
| ***A61P 35/00*** | (2006.01) |
| ***G01N 33/50*** | (2006.01) |
| ***G01N 33/68*** | (2006.01) |

(52) U.S. Cl.
CPC ............ *A61K 31/496* (2013.01); *A61P 31/18* (2018.01); *A61P 35/00* (2018.01); *G01N 33/5035* (2013.01); *G01N 33/6845* (2013.01); *G01N 2500/02* (2013.01)

(58) Field of Classification Search
CPC ........... G01N 33/5035; G01N 33/6845; A61K 31/496
See application file for complete search history.

(56) References Cited

U.S. PATENT DOCUMENTS

2016/0030566 A1 2/2016 De Silvestri
2016/0361298 A1* 12/2016 Novick ............. A61K 31/4178

FOREIGN PATENT DOCUMENTS

WO WO-2018226828 A2 * 12/2018 ........... A61K 31/192

OTHER PUBLICATIONS

Communication pursuant to Article 94(3) EPC issued for European Patent Application EP19783607.5, on Jan. 3, 2024, 8 Pages.

Germana Rappa et al: "Nuclear transport of cancer extracellular vesicle-derived biomaterials through nuclear envelope invagination-associated late endosomes", ONCOTARGET, vol. 8, No. 9, Feb. 28, 2017 (Feb. 28, 2017), pp. 14443-14461, XP055646926, DOI: 10.18632/oncotarget.14804.

Marion Weber-Boyvat et al: "OSBP-related protein 3 (ORP3) coupling with VAMPassociated protein A regulates R-Ras activity", Experimental Cell Research, vol. 331, No. 2, Feb. 1, 2015 (Feb. 1, 2015 ), pp. 278-291, XP055646938, Amsterdam, NL ISSN: 0014-4827, DOI: 10.1016/j.yexcr.2014.10.019.

Vesa M. Olkkonen: "OSBP-Related Protein Family in Lipid Transport Over Membrane Contact Sites", Lipid Insights, vol. 8(S1 ), Jan. 1, 2015 (Jan. 1, 2015 ), pp. 1-9, XP055646979.

Schwartz Ilan S et al: "Itraconazole and antiretroviral therapy: strategies for empirical dosing", Lancet Infectious Diseases, vol. 17, No. 11, Nov. 2017 (Nov. 2017), pp. 1122-1123, XP085271012, ISSN: 1473-3099, DOI: 10.1016/S1473-3099(17)30568-6.

(Continued)

*Primary Examiner* — Theodore R. Howell
(74) *Attorney, Agent, or Firm* — RC Trademark Company

(57) ABSTRACT

The present disclosure relates generally to methods of inhibiting a tripartite VAP-A, ORP3 and Rab7 (VOR) protein complex in multicellular organisms, to methods of identifying agents which inhibit such complex and to the medical use of those agents. Inhibition of the VOR complex causes interference with at least one mechanism of intercellular communication, wherein the intercellular communication is mediated by receptor-ligand interaction and/or EVs, and viral infection involving the transport of endocytosed biomaterials to the nucleus of recipient cells.

5 Claims, 13 Drawing Sheets

(56) References Cited

OTHER PUBLICATIONS

Mark F. Santos et al: "VAMP-associated protein-A and oxysterol-binding proteinrelated protein 3 promote the entry of late endosomes into the nucleoplasmic reticulum", Journal of Biological Chemistry, vol. 293, No. 36, Jul. 17, 2018 (Jul. 17, 2018), pp. 13834-13848, XP055646987, ISSN: 0021-9258, DOI: 10.1074/jbc.RA118.003725.

* cited by examiner

INHIBITION OF A TRIPARTITE VOR PROTEIN COMPLEX IN MULTICELLULAR ORGANISMS

TECHNICAL FIELD

The present disclosure relates generally to methods of inhibiting a tripartite VAP-A, ORP3 and Rab7 (VOR) protein complex in multicellular organisms, to methods of identifying agents which inhibit such complex and to the medical use of those agents. The invention further relates to an inhibitor of a tripartite VAP-A, ORP3 and Rab7 (VOR) protein complex for use in medicine. The present disclosure further relates to the use of Itraconazole or an Itraconazole analogue for the prevention or treatment of carcinoma and infectious diseases. Specifically, the present disclosure relates to Itraconazole or an Itraconazole analogue or salts thereof for use in inhibiting a tripartite VAP-A, ORP3 and Rab7 (VOR) protein complex in multicellular organisms. The present disclosure further relates to the use of the aforesaid compound to execute the aforesaid method.

BACKGROUND

Cancer and certain viral diseases (such as, HIV) are among the leading causes of fatal illness, with millions of deaths due to such diseases worldwide.

Despite the rapid advances in biomedical sciences, the practices employed for the treatment of such fatal diseases are still inadequate in many cases. Traditionally, many immunotherapeutic strategies are being explored to combat cancer, viral infections and age-related diseases. Treatments based on chemotherapy may be employed for curing Cancer. One approach is the inhibition of the process of cell multiplication, killing dividing cells by mutilating the control center (namely, nucleus) of such dividing cells or by interrupting the chemical processes involved in cell division.

Antiretroviral (ARV) therapy may be employed for curing viral diseases such as HIV. Typically, such ARV therapy employs microbes that target affected cells at different phases of their life cycle. Subsequently, such microbes inhibit cell fusion by preventing the virus from entering or by preventing the copying of Viral RNA into DNA and further block the virus from integrating or duplicating. However, these practices have severe limitations such as fluctuations in the molecular composition of the involved cells, challenges in defining the composition of the involved cells, low level of membrane expression of the requisite peptide complexes, presence of immunosuppressive cytokines converting the cells into a tolerogenic state and problems regarding storage and stability management.

Conventionally, antiangiogenic agents are used to treat certain cancers, alone or in combination with traditional cytotoxic drugs. However, tumors are highly adaptable. Consequently, the tumors may become resistant to such cytotoxic drugs and radiation. Furthermore, in some animal models, these treatments even make the tumors more aggressive, leading to advanced stages of the disease, such as advanced cancer, metastatic cancer and so forth. In other words, responses to such practices (such as, chemotherapy, AVP therapy and so forth) may be transient and may lead to development of drug resistance. Consequently, the effectiveness of such medications in curing the disease, decline drastically.

There exists a need to overcome the aforementioned drawbacks associated with the conventional practices for curing diseases such as Cancer and viral diseases.

SUMMARY

The present disclosure provides a method of inhibiting a tripartite VAP-A, ORP3 and Rab7 (VOR) protein complex in multicellular organisms, the inhibition causing interference with at least one mechanism of:

(a) intercellular communication, wherein the intercellular communication is mediated by receptor-ligand interaction and/or EVs; or (b) viral infection involving the transport of endocytosed biomaterials to the nucleus of recipient cells.

The aforesaid method of inhibiting a tripartite VOR protein complex, as disclosed in the present disclosure, provides a new molecular target. This new target is highly important as it provides a new approach to the therapy of a plurality of diseases including Cancer and Viral diseases. Moreover, the present disclosure provides ways to inhibit a VOR ternary complex in the nuclear compartment of the cell(s). Typically, such VOR complex enables the penetration of endosomes containing EVs or other infectious virus into the nucleus of healthy cell(s). Beneficially, the present disclosure provides a therapeutic approach that targets intercellular communications, for example, the intercellular communication between a tumor and hosts in the case of cancer. Typically, disruption of such intercellular communications between cell(s) affected by a disease and host(s) of the disease may be a powerful and fruitful strategy to combat the disease. Furthermore, since intercellular communications are implicated in a plurality of other diseases, these disruptions thereby enable effective therapy of a plurality of other diseases.

Conventional cancer treatments tend to involve the use of drugs that target the affected cells for curing the disease. Our new approach involves the disruption of the tripartite VOR protein complex assembly implicated in intercellular communication, which assists transport of the disease-causing materials into the nucleus of healthy cells. This approach helps overcoming the problem of drug resistance since the affected cells are not directly targeted. Furthermore, the inability to develop drug resistance by the cells affected by the disease prevents or slows down the development of advanced stages of the disease.

Optionally, inhibition of the tripartite VOR protein complex results from suppression or inhibition of at least one member of the tripartite VOR protein complex.

Optionally, inhibition of the tripartite VOR protein complex results from suppression or inhibition of the interaction between VAP-A and ORP3, ORP3 and Rab7, Rab7 and VAP-A, VAP-A and any member of the OSBP family, and/or any member of the OSBP family and Rab7.

Optionally, the tripartite VOR protein complex is inhibited by interaction of the tripartite VOR protein complex with at least one of a chemical agent or a biological agent, and/or by silencing at least one member of the tripartite VOR protein complex.

Optionally, the tripartite VOR protein complex is inhibited using a tripartite VOR protein complex inhibitor agent.

Optionally, the invention provides a method for identifying a chemical agent which inhibits the tripartite VOR protein complex, wherein the method comprises contacting at least one eukaryotic cell having the tripartite VOR protein complex with the chemical agent under conditions suitable for binding, and detecting the integrity of the tripartite VOR protein complex and/or consequence of the loss of the tripartite VOR protein complex.

The invention further provides a method for identifying a VOR protein complex inhibitor chemical agent for use as a pharmaceutical agent or as a lead compound, wherein the method comprises screening one or more chemical agents and determining their ability to inhibit the tripartite VOR protein complex.

Optionally, the method comprises determining the specific activity of a chemical compound (an identified chemical compound or compounds) for inhibiting the tripartite VOR protein complex, and wherein the method further comprises:

measuring the integrity of the tripartite VOR protein complex;

determining the consequences of loss of the tripartite VOR protein complex in response to:

a) presence/absence of the chemical agent; and b) external stimuli, wherein the external stimuli include at least one of extracellular vesicles (EVs), viruses, ligands.

Optionally, the method for screening a chemical agent comprises:

(a) infecting the recipient cells in well plates with at least one of VSV-G-pseudotyped HIV-1 NL4-3 Gag-iGFP deltaEnv Non-Infectious Molecular Clone or similar fluorescent viruses;

(b) contacting at least one identified chemical agent with the recipient cells for identifying the one or more lead compounds which strongly decreases fluorescence of a recipient cell population compared to a mock control, wherein the identified chemical agent is derived from screening of small molecule libraries and selected compounds associated with the recipient cell; and (c) adding a vital dye to exclude the recipient cells that are non-selectively damaged by the one or more lead compounds before the automatic imaging.

Optionally, the method for screening a chemical agent further comprises:

(a) isolating EVs from any cell line, which has been engineered to express Cre recombinase protein fused in-frame to CD9 or to another protein that gets transported into the nucleus upon internalization of EVs by recipient cell;

(b) adding the modified EVs that contain the Cre recombinase-CD9 fusion protein to any cell lines harboring cre-loxP sites, which would drive after recombination the expression of fluorescent reporter gene;

(c) pre-incubation of recipient cells with chemical agents that would block and/or interfere with VOR complex activity, i.e. leading to the inhibition of nuclear transfer of EV-derived materials notably Cre recombinase-CD9 fusion protein. With this setting, compounds that block the EV-mediated activation of fluorescent reporter protein by recipient cells are screened.

Optionally, the method includes using the tripartite VOR protein complex as a molecular target for the screening of chemical agents for their ability to inhibit the tripartite VOR protein complex.

Optionally, the recipient cell is carcinogenic. Preferably, the carcinogenic cell is at least one of a kidney carcinoma, a bladder carcinoma, an endometrial carcinoma or a head and neck carcinoma. Specifically, inhibiting the tripartite VOR protein complex leads to prevention of cancer metastasis. In another aspect, inhibiting the tripartite VOR protein complex leads to the treatment of cancer metastasis.

Optionally, the recipient cell is a cell exposed to an infectious external stimulus. More optionally, the external stimulus is a virus. Specifically, the virus is HIV-1.

Optionally, the recipient cell is at least one of a stromal cell, an epithelia cell, a neuron, a cardiac cell, a pancreatic cell, a renal cell, a cone cell and an alveolar macrophage cell.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

In a further aspect, embodiments of the present disclosure relate to a tripartite VOR protein complex inhibitor agent for use in medicine. Typically, such inhibition causes interference with at least one mechanism of:

(a) intercellular communication, wherein the intercellular communication is mediated by receptor-ligand interaction and/or EVs; and (b) viral infection involving the transport of endocytosed biomaterials to the nucleus of recipient cells.

The present invention further relates to a tripartite VOR protein complex inhibitor agent for use in the treatment or prevention of a disease or condition in which the tripartite VOR protein complex is implicated. Such diseases or conditions include but are not limited to cancer, cancer metastasis, infectious diseases (such as those caused by a virus, for example the HIV-1 virus), neurodegenerative diseases, a ventricular hypertrophy, type I diabetes, type II diseases, macular degeneration and lung diseases. Preferably the inhibitor is for use in the treatment at least one of a kidney carcinoma, a bladder carcinoma, an endometrial carcinoma, head and neck cancer.

In another embodiment, the present invention relates to a method of treatment or prevention of a disease or condition in which the tripartite VOR protein complex is implicated, by administration of a tripartite VOR protein complex inhibitor agent to a patient in need.

In a further aspect, the present disclosure seeks to provide a therapeutic use of Itraconazole or an Itraconazole analogue for treatment of cancer and infectious diseases.

Moreover, the present disclosure provides a method of inhibiting a tripartite VAP-A, ORP3 and Rab7 (VOR) protein complex in multicellular organisms for the treatment of cancer and infectious diseases.

In a further aspect, embodiments of the present disclosure relate to the use of Itraconazole or salts thereof or an Itraconazole analogue or salts thereof for inhibiting a tripartite VAP-A, ORP3 and Rab7 (VOR) protein complex in multicellular organisms by interfering with at least one mechanism of:

(a) intercellular communication, wherein the intercellular communication is mediated by receptor-ligand interaction and/or EVs; and (b) viral infection involving the transport of endocytosed biomaterials to the nucleus of recipient cells.

In a further aspect, embodiments of the present disclosure relate to the use of Itraconazole or salts thereof or an Itraconazole analogue or salts thereof for inhibiting a tripartite VAP-A, ORP3 and Rab7 (VOR) protein complex in multicellular organisms, the inhibition causing interference with at least one mechanism of:

(a) intercellular communication, wherein the intercellular communication is mediated by receptor-ligand interaction and/or EVs; or (b) viral infection involving the transport of endocytosed biomaterials to the nucleus of recipient cells.

An advantage of the present invention is the provision of an orally administrable compound for the inhibition of a tripartite VOR protein complex in the treatment of cancer and infectious diseases.

Optionally, the Itraconazole analogue is an analogue in which the sec-butyl chain of the Itraconazole has been replaced by a straight or branched C1-C10 alkyl chain.

According to the invention, Itraconazole, the itraconazole analogue or a salt thereof is for use in the treatment or prevention or a disease or condition in which the tripartite VOR protein complex is implicated.

In an embodiment, Itraconazole, an itraconazole analogue or a salt thereof is for use in the therapy, treatment and/or prevention of cancer and preferably cancer metastasis. More preferably, the cancer includes at least one of a kidney carcinoma, a bladder carcinoma, an endometrial carcinoma and/or head and neck cancer.

An aspect of the invention provides Itraconazole, an itraconazole analogue or a salt thereof for use in the treatment or prevention of an infectious disease. Preferably, the disease is caused by a virus. In a preferred embodiment the virus is HIV-1.

The present invention also provides Itraconazole, an itraconazole analogue or a salt thereof for use in the treatment or prevention of at least one of a neurodegenerative disease, a ventricular hypertrophy, type I diabetes, type II diabetes, macular degeneration and a lung disease.

A better understanding of the present invention may be obtained through the following examples which are set forth to illustrate but are not to be construed as limiting the present invention.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1A:
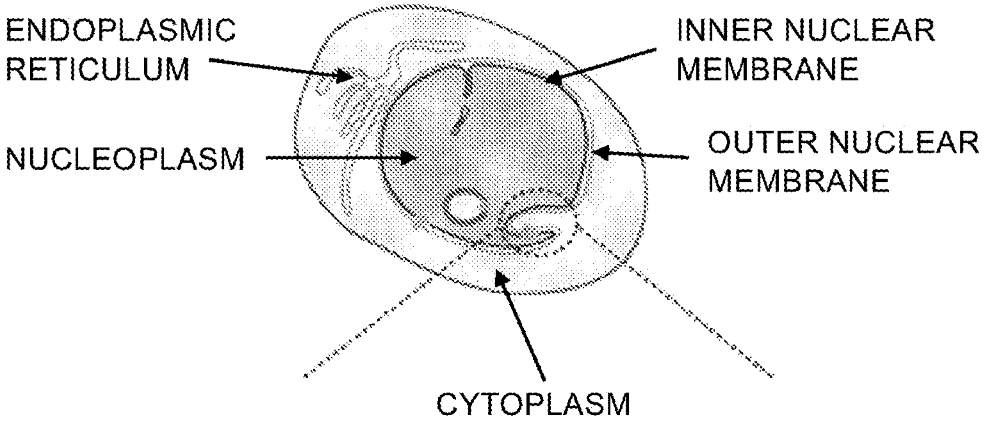
FIGS. 1A, 1B, and 1C are schematic illustration data showing a tripartite structure and localization of a VOR complex.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

Throughout the present disclosure, the term "multicellular organism" used herein relates to organisms (eukaryotic) with more than one cell, such as humans, animals, plants, fungi, algae and the like. The multicellular organisms are much larger and complex as compared to the unicellular organisms (with only one cell). Due to various cells, the multicellular organisms have a competitive advantage in terms of lifespan, growth, specialization, division of labor, efficiency and so forth. The functional aspects of the multicellular organisms often require the cells to be independent yet integrated to varying degrees. In other words, the multicellular organisms grow in size and number (or reproduce), metabolize nutrients and react to stimuli to perform efficiently in one or more processes of life. Nonetheless, various cells are dependent on each other and interact to perform specialized functions.

Specifically, the cells interact with each other through intercellular communication. The intercellular communication relates to communication between two or more cells. It may be appreciated that during the course of evolution, the multicellular organisms have developed various intercellular communication strategies, including but not limited to cell-cell contact, soluble molecules, quorum sensing, EVs, and so forth. Furthermore, the intercellular communication enables reception, transduction and response generation in the presence of stimuli, such as a water soluble signaling molecule, an antigen, a chemical substance and so forth. Nonetheless, it will be appreciated that intercellular communications expose the multicellular organisms to a higher risk of cancer or pathogenesis.

As mentioned previously, the intercellular communication is mediated by various means and are well-known to a person skilled in the art. Optionally, the intercellular communication is carried out by release of an intercellular communication messenger by cells of the recipient cell population. Specifically, the intercellular communication messenger of one recipient cell population interact with the cells of another recipient cell population to mediate the cell-cell interaction or the intercellular communication. The intercellular communication messengers include, but are not limited to, growth factors, cytokines (such as interleukins (IL), interferons (IFNs), tumor necrosis factors (TNFs) and the like), hormones, exomes and so forth.

In an example, the intercellular communication messenger, such as a cytokine, released by a cell of a first recipient cell population may induce a direct communication comprising modulation of a second recipient cell population in response to presence or absence of a modulator or intercellular communication between two or more cells. Additionally, alternatively, cytokine released by the cell of a third recipient cell population may induce an indirect communication comprising modulation of the second recipient cell population in response to: a modulator, a direct communication between the cytokine releasing cells of the third recipient cell population with that of the cytokine releasing cells of the first recipient cell population, or a combination thereof.

The modulator is a compound interacting, either directly or indirectly, with one or more cells in order to alter the intercellular communication or cell-cell interaction. Optionally, the modulator is at least one of a biological entity, a chemical entity, a physical entity, environmental stimuli, and the like. More optionally, the modulators include, but are not limited to, growth factors, cytokines, drugs, ions, neurotransmitters, hormones, adhesion molecule, antibodies, natural compounds, proteins, carbohydrates, interferons (IFN), antigen presenting cells (APC), T cell modulators, B cell modulators, Superantigens (SAg), toll-like receptor (TLR) modulators, combinations of modulators (such as CD3/CD28 agonists), and so forth. Furthermore, the activation or deactivation of the intercellular communication or cell-cell interaction in the presence of the modulator is measured relatively as a percentage or a fold increase or decrease in activation of an activatable entity within the cells of various recipient cell populations. In an example, the modulator, for example an antigen presenting cell (APC) such as, a dendritic cell or a macrophage, does not interact (or does not substantially interact) with the recipient cell population, such as T-cells or B-cells. Nonetheless, other types of modulators are also possible such as T cell activator (TCR), for example which interact with one type recipient cell population (such as T cells) but do not interact with any other type of recipient cell population (such as B cells) present in a culture of cells. The term "activatable entity" used herein relates to an entity that occurs in at least two distinguishable states, such as either in ON or OFF state. Optionally, the activatable entity forms a part of the recipient cell, for example, a site associated with a cellular protein, lipid, carbohydrate, or other constituent of the recipient cell. In an example, an activatable entity, such as a phosphorylatable site on a protein may be in its ON (or active) state only when phosphorylated. In an embodiment, the activatable entity may be activated in response to chemical additions and physical and biological modifications such as acetylation, acylation, dephosphorylation, glycosylation, hydrolysis, isomerization, methylation, nitration, phosphorylation, and so forth. In another example, the activatable entity is a protein that can be activated by internal or external stimuli, such as a change in its conformation, binding affinity, translocation, cleavage, and so on.

Throughout the present disclosure, the term "recipient cell" used herein relates to at least one cell receiving information (biomaterial) from a donor cell, wherein the biomaterial can be EVs, soluble ligands internalized with their plasma membrane receptor or virus. The donor cell type is a more transformed cell as compared to the recipient cell. Typically, the recipient cell is a somatic cell, preferably derived from a human. The recipient cells include, but do not limit to, blood cells, mesenchymal stromal cells, bone cells, muscle cells, epithelial cells, endothelial cells, immune cells, dendritic cells, somatic cells, germ cells, cells derived from various organs (such as pancreas, lungs, stomach, heart, spleen, kidney, thymus, cornea, bladder, esophagus and so forth), and so on. Typically, the donor cell is a transformed cell such as a cancer cell or infected cell. Donor cell can also be healthy cell communicating with transformed cell.

In an embodiment, the recipient cell receives (biomaterial) from a donor cell, wherein the biomaterial can be EVs, soluble ligands internalized with their plasma membrane receptor or virus, but not limited to it. In another embodiment, the recipient cell and the donor cell are derived from same species or different species from the same genus. In yet another embodiment, the recipient cell receives whole or part of constituents from at least one of: a chemical compound, a chemotherapeutic compound, a drug and the like, by contacting or mixing together the recipient cell with the at least one of: a chemical compound, a chemotherapeutic compound, a drug and the like.

The term "recipient cell population" used herein relates to a group of cells with same cell-type or same characteristic. Specifically, recipient cell population comprises cells with the same or substantially the same set of surface markers (such as transcription factors, proteins, fluorescent markers) specific to a cell type, wherein such set of surface markers are known in the art. In an example, a recipient cell population is a stem cell population, and various subpopulations of the stem cell, such as embryonic stem cells, cardiac stem cells, hematopoietic stem cells and so on are characterized by different sets of cell surface markers. For example, the embryonic stem cells have Oct-4 (or Oct-3 or Oct-3/4) markers and the hematopoietic stem cells have CD34, CD133, ABCG2 and Sca-1 markers.

The term "culture of cells" or "culture of recipient cell population" relates to cultures containing a plurality of recipient cell populations in communication. Optionally, the culture of cells is derived from at least one sample obtained from the multicellular organism. In an embodiment, the multicellular organism is a normal individual, specifically a mammal, more specifically a human. In another embodiment, the multicellular organism is an individual (namely, a patient) with a condition (such as cancer, AIDS, tuberculosis and so forth). The sample may be obtained once or multiple times from the multicellular organism, namely normal sample from the normal individual and pathogenic sample from the individual with a condition. Furthermore, the sample may be a single or multiple sample(s) obtained from different location of the body of the multicellular organism. The multiple samples include, but are not limited to fluid samples (such as blood sample, bone marrow sample, lymph node sample, urine sample, serum sample, DNA sample, saliva sample, stool sample, semen sample, tear sample, sputum sample, menstrual blood sample, amniotic fluid and so on), effusions (such as from joints, peritoneal cavity, heart, and so on), solid tissue samples (such as biopsies, tissue scrapings, surgical specimens, stem cells and so on), pathogenic cells (such as circulating tumor cells (CTC)) and so forth. In an embodiment, cells comprising different recipient cell populations are cultured in-vitro in a growth media (such as a human-derived serum, a fetal bovine serum, a bovine serum, a goat serum, a horse serum, and so on). Subsequently, the cultured cells are exposed to one or more modulators.

Typically, the intercellular communication is mediated by receptor-ligand interaction, wherein the ligand is a signaling molecule and receptor is a receiving molecule attached to the cell membrane that is specific for one (or a few) ligand(s). The receptor and ligand bind together by introducing functional and structural changes in the receptor that allows transmission of a signal through the recipient cell. Typical receptors include intercellular receptors and cell surface receptors occurring inside of the cell (such as in cytoplasm or nucleus) and in the plasma membrane respectively. The receptor-ligand interactions facilitate all biological processes occurring in unicellular or multicellular organisms.

Additionally, alternatively, intercellular communication is mediated by extracellular vesicles (indicated by "EVs" hereafter). Throughout the present disclosure, the term "extracellular membrane vesicles" used herein relates to small vesicles released from almost all types of multicellular organisms. Specifically, the EVs serve as effective means for intercellular communication. More specifically, EVs transfer specific bioactive molecules, comprising functional mRNAs and microRNAs (miRNAs) across cells for their translation into homologous or heterologous proteins. Additionally, EVs protect biomolecules from degradation while allowing exchange of proteins, lipids, nucleic acids and so on between the donor cell and the recipient cell. In an example, vesicles secreted by immune cells of central nervous system mediate intercellular communication between neurons, glia (or astrocytes) and microglia over long range distances. In another example, EVs associated with immune system allow exchange of antigen or major histocompatibility complex (MHC)-peptide complexes between antigen-bearing cells and antigen-presenting cells. For example, EVs secreted from B lymphocytes present MHC II-antigen complexes to T lymphocytes.

Furthermore, EVs are known to transport cytosolic material targeted for disposal out of the cells into the extracellular space. Typically, the cytosolic material includes, but is not limited to, (including proteins, lipids and RNAs). EVs are responsible for removing biomaterials that affect the cell at different sites and introducing the required supplements. For example, EVs are responsible for eliminating transferrin receptor and/or integrins from reticulocytes, which are not required by differentiated red blood cells.

It would be appreciated that the intercellular communication and the cytosolic waste management is mediated by two types of EVs, exosomes and microvesicles. The exosomes are small membrane-bound vesicles ranging from 30 to 100 nm in size and released from the cell surface by exocytosis.

Specifically, the exosomes result from invagination of the plasma membrane to generate early endosomes. The early endosomes subsequently invaginate to form intraluminal vesicles (ILVs) and multivesicular bodies (MVBs) that fuse with the plasma membrane to release mature ILVs, called exosomes, into the extracellular spaces. Typically, the exosomes mimic the molecular constituents of their cell of origin, and contain proteins, lipids, mRNAs, miRNAs and the like. The mRNAs are subsequently translated into functional proteins and miRNAs effect gene silencing in the recipient cells. Exosomes are also known to elicit biological effects due to the presence of surface receptors or ligands for selective interaction with specific targets ligands or receptors of target cells (donor cell or recipient cell). Furthermore, exosomes mediate transfer of molecules between two or more cells via membrane vesicle trafficking. In an embodiment, exosomes may also play a functional role in mediating transport of tumors and pathogens across cell, thereby affecting the immune system of the recipient cells. Therefore, it is a potential area of research to explain various biological processes associated with intracellular signaling and tumor growth and pathogenesis in a recipient cell, preferably mammalian cells, more preferably human cells. Generally, the EVs, especially the exosomes are influenced by the extracellular environment, however, the exosomes are highly stable in extracellular space due to the presence of relatively higher concentrations of cholesterol, sphingomyelin and detergent-resistant membrane domains in its lipid bilayer. Therefore, high stability of exosomes in bodily fluids makes them highly efficient as potential disease markers. In an example, exosomes derived from cancer cells may be analyzed in a blood plasma sample after a predefined period of incubation, for example such as 90 days.

Another class of EVs includes the microvesicles (MVs, also known as ectosomes). The microvesicles, such as apoptotic bodies, originate from the outward budding or fission of the plasma membrane of the cell. The microvesicles range from 0.1 to 1 μm in size. Microvesicles contain membrane proteins and phospholipids shed from various cell types. Like the exosomes, the microvesicles also play a functional role in intercellular communication and transport of biomaterial, such as proteins, mRNA and miRNA from one cell to another. In an embodiment, the microvesicles are known to play a primary role in transfer of pathogens and tumor antigens into the recipient cells. In another embodiment, microvesicles are released from the endothelial cells, smooth muscle cells, white blood cells, platelets and red blood cells leading to inflammatory and pathological diseases including, but not limited to, hypertension, cardiac ailments, neurodegenerative disorders, diabetes and rheumatoid arthritis. Additionally, changing levels of microvesicles in various diseases, for example such as cancer, rheumatoid arthritis, neurological disorder, makes it a potential biomarker in a variety of diagnostic analysis. In an example, Alzheimer's disease can be diagnosed in patients at a relatively early stage by measuring the increased levels of phosphorylated Tau proteins, or epilepsy is associated with increased levels of CD133 in microvesicles of the patients with epilepsy.

Furthermore, the EVs deliver the biocomponents through the nuclear membrane into nucleoplasm of the recipient cells. The nuclear membrane (or nuclear envelope) is a double lipid bilayer, comprising an inner nuclear membrane (INM) and an outer nuclear membrane (ONM), separated by a perinuclear space. Specifically, the nuclear membrane separates the nucleoplasm and cytoplasm of the cell. The nuclear membrane encloses various components, such as one or more nucleus, nucleoplasm, endoplasmic reticulum (ER), genetic material and the like, contributing to nuclear structural integrity of the cell. It will be appreciated that the lipid bilayer composition of the nuclear membrane also comprises other bioactive components, such as proteins, a network of invaginations, such as nucleoplasmic reticulum (NR), and so forth.

Specifically, the EV-derived biocomponents are delivered into the nucleoplasm of the recipient cells through small holes and/or channels called nuclear pores in the nuclear membrane. More specifically, the nuclear transfer of EV-derived biocomponents occurs through the nuclear pores. Furthermore, membrane protein and/or combinations thereof (namely, protein complexes) play a vital role in nuclear transfer of EV-derived biocomponents. Such protein complexes include, but are not limited to, a tripartite VAP-A, ORP3 and Rab7 (VOR) protein complex. Specifically, the tripartite VOR protein complex comprises an ER-localized vesicle-associated membrane protein-associated protein A (VAP-A), a cytoplasmic oxysterol-binding related protein 3 (ORP3) and a late endosome (LE)-associated small GTPase Rab7 in the NEI. More specifically, the tripartite VOR protein complex specifically localizes late endosomes (indicated by 'LE' hereafter) into the NR and are essential for the nuclear transfer of EV-derived components. Nonetheless, the components of the tripartite VOR protein complex is not only found in the NEI, but also widely distributed across the cytoplasm. Specifically, the VAP-A and Rab7 pair is distributed across the cytoplasm. Furthermore, interaction of the VAP-A with the ORP3 mediates the localization of the Rab7 into the ONM, where they interact with the nuclear pores and subsequently with the adjacent cells.

Moreover, VAP-A has a homologue, VAP-B, however, VAP-B is not required for the presence of LE in the NEI. Furthermore, silencing of VAP-B does not affect the expression of VAP-A. It is interesting to note that VAP-A is also associated with the presence of the ORP3 in the NEI. Specifically, the VAP-A interacts with the peripheral LE multi-domain oxysterol-binding protein (OSBP)-related protein 1L (ORP1L) that binds to small GTPase Rab7. It will be appreciated that silencing the binding of VAP-A to ORP3 prevents the association of Rab7+LE with the nuclear envelope invaginations (NEI), and hence, the transfer of endocytosed EV-derived components to the nucleoplasm of recipient cells.

Therefore, the inhibition of EV-mediated intercellular communication can have therapeutic potential in determining cancer and other diseases such as viral infection associated with a dysregulation of the EVs based on change in their values under pathological conditions. It will be appreciated that like any other cells, the cancerous cells also secrete EVs. Specifically, cancer cells (or the malignant tumor cells) secrete more EVs as compare to normal cells or benign tumor cells (counterpart of the malignant tumor cells). Furthermore, EVs secreted by cancerous cells are critical mediators of the intercellular communication between the cancerous cells and the recipient cells of the multicellular organisms. Typically, EVs facilitate various pathophysiological processes, such as coagulation, vascular leakage, pre-metastatic niche formation and metastasis at various sites in different tumor microenvironments. Therefore, by monitoring the change in levels of EVs, EVs serve as potential biomarkers and novel therapeutic targets against cancer progression and associated metastatic development. In an embodiment, EVs also serve as a potential vehicle for the delivery of therapeutic agents or drugs against cancer.

Furthermore, intracellular communication is also responsible for various pathological conditions, such as a viral infection and so forth. The viral infection involves the transport of endocytosed biomaterials to the nucleus of recipient cells. Specifically, like the cancerous cells, virus-infected cells also secrete EVs, thus large numbers of EVs are secreted during viral infection. Specifically, viral particles, proteins and RNA, are transferred from a viral cell into nucleus of the recipient cell via the microvesicles. Nonetheless, the viral cells also secrete virions along with the secretion of extracellular vesicles (microvesicles). Generally, the viruses are non-living organisms outside a host cell, however, they lead a normal reproductive live inside the host. In light of the aforesaid, the viral cells deploy both the EVs and the virions for transferring the viral biocomponents into the recipient cells. Majorly, the viral cells exploit the EVs to transport viral proteins (namely, Nef and Gag), fragments of viral genome (RNA) and viral miRNA to the genetic machinery of the recipient cell for sustainable growth of the viral biocomponents inside the multicellular organisms, thereby affecting the viral infection. In an embodiment, the EVs suppresses viral infection by attaching to viral particles thereby reducing the release of virions that infect immune cells of the recipient cells, such as $CD4^{+}$T cells.

In an embodiment, EVs serve as potential biomarkers and novel therapeutic targets against cancer and viral infection. In another embodiment, EVs also serve as a potential vehicle for the delivery of therapeutic agents or drugs against various diseases, such as cancer, and pathological conditions, such as viral infection, preferably AIDS.

The method of inhibiting a tripartite VAP-A, ORP3 and Rab7 (VOR) protein complex in multicellular organisms, the method comprising interfering with at least one mechanism of: intercellular communication, wherein the intercellular communication is mediated by receptor-ligand interaction and/or EVs; or viral infection involving the transport of endocytosed biomaterials to the nucleus of recipient cells, represents another aspect of the invention. In another aspect, inhibition of a tripartite VAP-A, ORP3 and Rab7 (VOR) protein complex in multicellular organisms causes interference with at least one mechanism of: intercellular communication, wherein the intercellular communication is mediated by receptor-ligand interaction and/or EVs; or viral infection involving the transport of endocytosed biomaterials to the nucleus of recipient cells.

Specifically, the method includes targeting the tripartite VOR protein complex to prevent the intercellular communication mediated by receptor-ligand interaction and/or EVs. Furthermore, the method also includes targeting the tripartite VOR protein complex to prevent the transport of endocytosed biomaterials to the nucleus of recipient cells. In an embodiment, the method comprises inhibiting the tripartite VOR protein complex which is associated with the transfer of cancer and viral infection to the recipient cell.

Optionally, the inhibition of the tripartite VOR protein complex results from suppression or inhibition of at least one member of the tripartite VOR protein complex. As mentioned previously, the tripartite VOR protein complex is composed of 3 proteins, VAP-A, ORP3 and Rab7. The interaction between at least two of these results in the intercellular communication and the transfer of biocomponents from the extracellular spaces into the nucleus of the recipient cell. Therefore, if any one member of the 3 proteins of the tripartite VOR protein complex is suppressed or inhibited then the formation of the tripartite VOR protein complex is blocked. For example, VAP-A interacts with ORP3 that binds with Rab7 in the NEI which facilitates transfer of EV-derived components to the nucleoplasm of recipient cells. More optionally, inhibition of the tripartite VOR protein complex results from suppression or inhibition of the interaction between VAP-A and ORP3, ORP3 and Rab7, Rab7 and VAP-A, VAP-A and any member of the OSBP family, and/or any member of the OSBP family and Rab7. As mentioned previously, the 3 components of the tripartite VOR protein complex interact with each other to facilitate the transfer of EV-derived components to the nucleoplasm of the recipient cells. Therefore, if any two members of the three proteins of the tripartite VOR protein complex are suppressed or inhibited then the formation of the tripartite VOR protein complex is blocked as the third protein is not able to function normally. For example, inhibition of the interaction between VAP-A and ORP3 prevents the binding of ORP3 and Rab7 in the NEI, which is essential for the transfer of the EV-derived components to the nucleoplasm of recipient cells.

Optionally, the tripartite VOR protein complex is inhibited by interaction of the tripartite VOR protein complex with at least one of a chemical agent, a biological agent, and silencing of the at least one member of the tripartite VOR protein complex. Generally, the tripartite VOR protein complex may be inhibited by interaction of the tripartite VOR protein complex with at least one of a chemical agent, a biological agent, and silencing of the at least one member of the tripartite VOR protein complex. Specifically, antibodies, peptides, aptamers and small interference (si) RNA block the VAP-A or ORP3. More specifically, the siRNA target VAP-A or ORP3 and inhibit the nuclear translocation of EV-derived proteins and nucleic acids. Similarly, a biological agent such as a fragment of DNA or a protein may be used to inhibit the interaction of the tripartite VOR protein complex Optionally, the tripartite VOR protein complex is inhibited using a tripartite VOR protein complex inhibitor agent. Specifically, the tripartite VOR protein complex is inhibited using a tripartite VOR protein complex inhibitor agent, such as a drug, a chemical agent, a pharmaceutical compound, a biological material, and so forth.

Optionally, for identifying a chemical compound which inhibits the tripartite VOR protein complex, wherein the method comprises contacting at least one eukaryotic cell having the tripartite VOR protein complex with the chemical compound under conditions suitable for binding, and detecting the integrity of the tripartite VOR protein complex and/or consequence of loss of the tripartite VOR protein complex. Since, nuclear transfer of biomaterials is mediated by either the receptor-ligand interactions and/or EVs, allowing the tripartite VOR protein complex to bind to the chemical compound in suitable conditions of growth. The interaction of the tripartite VOR protein complex and the chemical compound may increase the integrity of the tripartite VOR protein complex and/or lead to the disintegration of the tripartite VOR protein complex.

Optionally, for identifying a VOR protein complex inhibitor chemical compound for use as a pharmaceutical agent or a lead compound, wherein the method comprises screening one or more chemical agents and determining their ability to inhibit the tripartite VOR protein complex. Specifically, the chemical compound is screened from the available plurality of data sources over the internet. In an embodiment, the chemical compound may also be screened using known or selected compounds. For example, out of the selected compounds, drug A1 which is effective in disease D1 can also be screened to identify its function in disease D2. Therefore, a suitable inhibition activity of the chemical compound towards the tripartite VOR protein complex makes it a potential therapeutic agent against the tripartite VOR protein complex.

Optionally, the method comprises determining the specific activity of the identified chemical compound or compounds for inhibiting the tripartite VOR protein complex, and wherein the method further comprises: measuring the integrity of the tripartite VOR protein complex; determining the consequences of loss of the tripartite VOR protein complex in response to: presence/absence of the chemical agent and external stimuli, wherein the external stimuli include at least one of EVs, viruses, ligands. It will be appreciated that the receptor-ligand binding is a specific activity of two compounds that are intended to bind. The method is used to determine the specific activity of identified chemical compound for inhibiting the tripartite VOR protein complex. In such case, the integrity of the tripartite VOR protein complex is measured in response to activity of the tripartite VOR protein complex to still mediate the nuclear transfer of EV-mediated intercellular communication. Furthermore, it will be appreciated that if the chemical compound fails to specifically bound to the tripartite VOR protein complex, then no nuclear transfer of signals and/or biocomponents is feasible and thus results in consequence of loss in the VOR protein complex. In an embodiment, the specific activity of the chemical compound to in the presence or absence of the external stimuli. Optionally, the external stimuli include at least one of EVs, viruses, ligands. More optionally, the specific activity of the chemical compound in the presence of various factors, such as EVs, viruses and ligands determines the effect of the chemical compound in increasing or suppressing the transfer of signals and food.

Optionally, the method for screening the identified chemical compound comprises infecting the recipient cells in well plates with at least one of VSV-G-pseudotyped HIV-1 NL4-3 Gag-iGFP deltaEnv Non-Infectious Molecular Clone or similar fluorescent viruses. In the presence of an external stimuli, for example such as a virus, the recipient cell is immobilized on the assay plate. Optionally a 6- or 96- or 384-well plate is used. The method further comprises contacting at least one identified chemical compound with the recipient cells for identifying the one or more lead compounds which strongly decreases fluorescence of a recipient cell population compared to a mock control, wherein the identified chemical compound is derived from screening of small molecule libraries and selected compounds associated with the recipient cell. The term "lead compound" used herein relates to a pharmaceutically active component, like a drug, or an antibody or a protein that brings about structural and functional changes in the target or the recipient cell. For example, a lead compound may be a drug that is selective against cancer and inhibits the progression of cancer from one part of the body to another.

The term "mock control" used herein relates to a reference point which is compared with the sample test. Generally, a mock control comprises the basic cell, for example a recipient cell, but lacks the any additives, such as a virus or drug or a fluorescent dye in the culture plate.

It will be appreciated that the fluorescence of the recipient cell-virus complex will be higher in the well of assay plate, however, addition of chemical compound leads to decrease in the fluorescence level on the assay plate. Specifically, contacting the at one or more chemical compound with the recipient cell to identify the lead compound or the identified chemical compound to study the effect of external stimuli. The method further comprises adding a vital dye to exclude the recipient cells that are non-selectively damaged by the one or more lead compounds before the automatic imaging. Specifically, the vital dye are the dyes specific to staining of the nuclear membrane. Hence, addition of vital dye enables in distinguishing between cells with intact nuclear membrane and the ones with disrupted nuclear membrane. More specifically, only the cells with a disrupted nuclear membrane are selected to screen the lead compounds.

Optionally, a fluorescent vital dye, such as 7-aminoactinomycin D (7-AAD) is used. 7-aminoactinomycin D (7-AAD) dye exhibits fluorescence different from that of green fluorescent protein (GFP). Furthermore, 7-AAD possess a strong affinity for the DNA and does not pass through intact cell membranes. Therefore, 7-AAD successfully labels cells that lose the plasma membrane integrity such as apoptotic and dead cells. Subsequently, both fluorescence (i.e. 7-AAD and GFP) is measured simultaneously by a fluorescent plate reader or imaging flow cytometer with appropriate wavelength filters to distinguish them.

In an embodiment, the vital dye and the associated fluorescent intensity is measured using a fluorescent microplate reader or a multi-detection microplate reader. The fluorescent microplate reader or a multi-detection microplate reader instrument is designed for screening and drug discovery. It further requires repeated absorbance measurements of fluorescent-tagged molecules (e.g., proteins, nuclei acids). In another embodiment, an imaging flow cytometer may be employed to measure the fluorescent intensity of the assay plate. The imaging flow cytometer combines the speed, sensitivity and phenotyping abilities of flow cytometry with a detailed imagery of microscopy at the level of a single cell.

The term 'imaging' relates to representation or creation of an object/scene by recording light/electromagnetic radiations emanating from the object, by means of emission or reflection. More specifically, a real image is produced on an image-sensing surface inside an imaging device during a timed exposure. Typically, the image-sensing surface comprises an array of pixels arranged in color-filter units (or cells) for generating red, blue, green and white image signals.

It will be appreciated that imaging performed by using time-lapse video micrography comprises acquiring video every 20 seconds for about 5 minutes using a Nikon $A1R^{+}$ confocal microscope. Other time windows can be used. Specifically, the time-lapse video micrography requires an optimum temperature (for example 37° C.) and carbon dioxide (5%) concentration, in order to capture the growth process of the cells in real-time. Furthermore, the time-lapse video micrography is used for still images, by way of acquiring images every 10 seconds for 10 minutes.

However, imaging could be performed using various other means including but not limited to a high-dynamic-range imaging device, a low-dynamic-range imaging device, a digital camera. Embodiments of the disclosure employ a high-dynamic-range (indicated by 'HDR' hereafter) imaging device. Specifically, the HDR imaging employs combining two or more images to produce a greater range of luminance in a final image as compared to standard digital imaging techniques. More specifically, HDR imaging employs taking several images with different exposures and then merging the images into a single HDR image. In an example, the different exposures may be −1 EV, 0 EV and +1 EV. Beneficially, HDR imaging employs a suitable HDR software that enables high sensitivity, excellent measuring range, higher luminance, minimized risk of saturation of sensor, tone mapping, much greater range of colors and brightness, image alignment, filtering random noise, and so forth.

In an embodiment, the method for screening the identified chemical agent may further include isolating EVs from any cell line. Specifically, isolating EVs from been engineered to express Cre recombinase protein fused in-frame to CD9 or to another protein that gets transported into the nucleus upon internalization of EVs by recipient cell. Further, the method may include adding the modified EVs that contain the Cre recombinase-CD9 fusion protein to any cell lines harboring cre-loxP sites, which would drive after recombination the expression of fluorescent reporter gene. The method further includes pre-incubation of recipient cells with chemical agents that would block and/or interfere with VOR complex activity, i.e. leading to the inhibition of nuclear transfer of EV-derived materials notably Cre recombinase-CD9 fusion protein. With this setting, we will screen for compounds that block the EV-mediated activation of fluorescent reporter protein by recipient cells. In this embodiment, the fluorescent reporter gene may include but not limited to GFP or other fluorescence proteins. Further, "floxed stop" strategy or "double-inverse orientation/Flex construct" strategy can be used to create reporter recipient cell line. Upon recombination, nucleus/cytoplasm of recipient cells will be highlighted by the expression of GFP. The latter can be monitored using fluorescent microplate reader/Multi-detection microplate reader or imaging flow cytometer.

Optionally, the method includes using the tripartite VOR protein complex as a molecular target for the screening of chemical agents for their ability to inhibit the tripartite VOR protein complex. Specifically, the chemical agents are targeted at the tripartite VOR protein complex to identify the specificity of the chemical agents and the tripartite VOR protein complex.

Optionally, the recipient cell is carcinogenic. The method for determining the inhibition of the tripartite VOR protein complex comprises receiving a recipient cell, wherein the recipient cell can be a cancerous cell. Specifically, the recipient cell or the carcinogenic cell is selected from at least one of a kidney carcinoma, a bladder carcinoma, an endometrial carcinoma or a head and neck carcinoma. In an embodiment, the recipient cell is at least one of a stromal cell, epithelial cell, a neuron, a cardiac cell, a pancreatic cell, a renal cell, a cone cell and an alveolar macrophage cell. Optionally, inhibiting the tripartite VOR protein complex leads to prevention of cancer metastasis. Optionally, the recipient cell is infectious external stimuli. More optionally, the external stimulus is a virus. Further, optionally, the virus is HIV-1.

The present disclosure provides a compound selected from Itraconazole or an Itraconazole analogue or salts thereof for use in inhibiting a tripartite VAP-A, ORP3 and Rab7 (VOR) protein complex in multicellular organisms by interfering with at least one mechanism of intercellular communication, wherein the intercellular communication is mediated by receptor-ligand interaction and/or EVs; and viral infection involving the transport of endocytosed biomaterials to the nucleus of recipient cells is provided. Generally, Itraconazole, a regulatory (such as FDA) approved azole antifungal drug, is used to treat a variety of fungal infections. Specifically, Itraconazole inhibits the growth of fungi. More specifically, it prevents the fungi from producing the membrane that surrounds the fungal cells. However, Itraconazole has a broader spectrum of activity than just as an antifungal agent. Specifically, Itraconazole inhibits the tripartite VOR protein complex by either interfering with the mechanism of intercellular communication mediated by the receptor-ligand interaction and/or the EVs, and/or transport of endocytosed biomaterials to the nucleus of recipient cells. More specifically, Itraconazole prevents the binding of Rab7 to ORP3, thereby blocking penetration of $Rab7^{+}$ late endosomes containing EVs or HIV-1 virus into the nuclear envelope invaginations and thus the transfer of their biocomponents into the nucleus. Furthermore, the Itraconazole analogs or any modifications of its molecules, such as its salts, may be more specific and potent inhibitors as anti-cancer and anti-viral drugs.

Optionally, the method comprises an Itraconazole analogue, wherein the Itraconazole analogue is an analogue in which the sec-butyl chain of the Itraconazole has been replaced by another group (R). The R group may be selected from a range of groups, including alkyl, aryl, cycloalkyl, heteroaryl, heterocycle, alkenyl, alkenylene, alkynyl or alkynylene. Preferably R is a straight or branched C1-C10 alkyl. The Itraconazole or itraconazole analogue of the invention includes all possible enantiomers and diastereoisomers of Itraconazole and salts thereof.

Optionally, the method comprises the Itraconazole, an itraconazole analogue or a salt thereof for use in the treatment or prevention or a disease or condition in which the VOR complex is implicated. Specifically, the Itraconazole, an itraconazole analogue or a salt thereof is used to inhibit the tripartite VOR protein complex associated with disease such as cancer or condition such as viral infection. As mentioned previously, the Itraconazole, an itraconazole analogue or a salt thereof is a potential anti-cancer and anti-viral agent, therefore it is use in the treatment or prevention or a disease or condition in which the VOR complex is implicated.

Optionally, the method comprises the treatment and prevention of cancer and cancer metastasis. Specifically, cancer is caused due to cancerous cells (or carcinoma or carcinogenic cells or tumors), especially the malignant cancer/tumor cells. The counterpart of the malignant cancer/tumor cells are benign tumor cells that do not cause cancer. More specifically, the cancerous cells possess potential to invade the neighboring cells and spread over different parts of the body of a multicellular organism. Specifically, diseases like cancer are characterized by an unregulated cell growth. The growth of cancer involves various stages including, but not limited to, pre-metastatic niche formation and metastasis at various sites in different tumor microenvironments. Cancer metastasis refers to the regional growth of cancer, i.e. the potential of cancerous cells to spread from one part to another and in the process arranging for resources (from the host cell) supporting its growth. Therefore, the present method comprises the use of potential anti-cancer agents against the invasion of the recipient cell by the cancer cells.

Optionally, the cancer includes at least one of a kidney carcinoma, a bladder carcinoma, an endometrial carcinoma, head and neck cancer. However, according to the Human Protein Atlas, ORP3, the direct target of itraconazole in the VOR complex, is highly expressed in kidney, bladder and endometrium, the organs of origin of kidney, bladder and endometrial carcinomas. The treatment of these types of cancer is novel not only because Itraconazole has never been clinically tested before on the above-cited types of cancers but also because Itraconazole has been previously studied on other types of cancer as inhibitor of Hedgehog or other types of pathways, but not as inhibitor of the VOR complex. More optionally, the kidney carcinoma attacks the kidney cells of the multicellular (host) organism and remain confined to the kidneys. The bladder carcinoma attacks the urinary bladder in the host organism. Specifically, the bladder carcinoma starts invariably from the inner layer of the bladder and invade further into the adjacent layers. Furthermore, the bladder carcinoma possesses the ability to spread to other body parts, including the lungs, bones, liver, and so on. It may be noted that the bladder carcinoma is more common in males as compared to females. Further, the endometrial carcinoma starts with the uterus, specifically at the lining (endometrium) of the uterus. Endometrial carcinoma can be treated by surgically removing the uterus. Head and neck cancers usually begin in the squamous cells lining the moist and mucosal surfaces inside the head and neck, such as mouth, nose, throat, larynx, sinuses, salivary glands and so on.

In an embodiment, the cancer may include other types of cancers including, but not limited to, melanoma, breast cancer, lung cancer, blood cancer, colorectal cancer, oral (or oropharyngeal) cancer, prostate cancer, thyroid cancer, uterine cancer, and so on.

Optionally, the method further comprises the Itraconazole, an itraconazole analogue or a salt thereof for the treatment or prevention of an infectious disease. Specifically, such infectious disease is due to a pathological condition. More specifically, the pathological condition or the infectious disease may be caused due to various pathogens including, but not limited to, a bacterium, a virus, a fungus, a protozoan, and so forth. The treatment or prevention of the infectious disease requires targeting the pathogen, the bacteria, the virus, the fungus and/or the protozoan. Treatment of these diseases with Itraconazole is novel because Itraconazole has been previously used only in fungal diseases as an inhibitor of ergosterol biosynthesis, not as an inhibitor of the VOR complex.

Optionally, the disease is caused by a virus. A virus is a small infectious agent. Generally, viruses are non-living organisms outside a host cell, however, they lead a normal reproductive live inside the host. Specifically, the virus replicates only inside the living cells of other organisms, such as animals, plants, humans, bacteria, and so forth. The viral infection involves the transport of endocytosed biomaterials to the nucleus of recipient cells. More optionally, the virus is HIV-1. The HIV-1 is a virus that attacks immune system of the host organism (or recipient cell), specifically CD-4 cells. HIV-1 causes a viral infection, namely AIDS, which severely damages the immune response of the host organism. Specifically, like the cancerous cells, virus-infected cells also secrete EVs, thus large numbers of EVs are secreted during viral infection. More specifically, viral particles, proteins and RNA, are transferred from a virus-infected cell into nucleus of the recipient cell via the EVs, especially the microvesicles. Nonetheless, the viral cells also secrete virions, along with the EVs, for transferring the viral biocomponents into the recipient cells. Majorly, the viral cells exploit the EVs to transport viral proteins (namely, Nef and Gag), fragments of viral genome (RNA) and viral miRNA to the genetic machinery of the recipient cell for sustainable growth of the viral biocomponents inside the multicellular organisms, thereby affecting the viral infection. In an embodiment, EVs serve as potential biomarkers and novel therapeutic targets against viral infection. In another embodiment, EVs also serve as a potential vehicle for the delivery of therapeutic agents or drugs against viral infections, such as AIDS. In yet another embodiment, the EVs suppresses viral infection by attaching to viral particles thereby reducing the release of virions that infect immune cells of the recipient cells, such as $CD4^{+}T$ cells. Nevertheless, HIV virus can counteract its inhibition by EVs by incorporating HIV-Nef into the EVs that decreases the host's antiviral response. Therefore, there exists means for inhibiting the intercellular communication that leads to progression of cancer and other pathological diseases such as AIDS or other viral infections.

In an embodiment, the method comprises using the Itraconazole or an Itraconazole analogue or salts thereof for the treatment of at least one of a neurodegenerative disease, a ventricular hypertrophy, a type I diabetes, a type II disease, a macular degeneration and a lung disease. The EV-mediated intercellular communication is also implicated in various conditions including, but not limited to, neurodegenerative disease, a ventricular hypertrophy, a type I diabetes, a type II disease, a macular degeneration and a lung disease. Typically, the neurodegenerative disease includes Alzheimer's disease, Parkinson's disease and so on. Specifically, the neurodegenerative diseases target the neurons or nerve cells in the brain. Similarly, the ventricular hypertrophy, the type I diabetes and/or type II disease, the macular degeneration and the lung disease are associated with specific cell types, such as a cardiac cell, a pancreatic cell, a renal cell, a cone cell and an alveolar macrophage cell. Furthermore, the EVs contain various associated proteins specific for a viral disease. For example, the EVs contain neurodegenerative disease associated proteins including a prion protein, a beta amyloid, an alpha-synuclein, a tau protein and the like.

Optionally, the Itraconazole or an Itraconazole analogue or salts thereof may be consumed orally or administered intravenously. However, other suitable route of administration can be employed. For example, transdermal, topical, parenteral, ocular, vaginal, rectal, buccal, lingual, intranasal and inhalation. For the purpose of the present invention, the Itraconazole or an Itraconazole analogue or salts thereof may be preferably administered by the oral route. Specifically, the oral administration of the Itraconazole includes but is not limited to capsules, tablets, powders, pellets, syrups, concoctions, and so on.

Furthermore, the dose of the Itraconazole depends on various parameters, such as the nature and degree of the condition, body weight, age, general health, diet followed, gender, frequency of administration, duration of treatment, any other drug prescribed or consume, and so forth. The frequency of administration may range from once, twice or more often each day. Additionally, the duration of treatment relates to the total amount of time for which the treatment is provided. Optionally, the Itraconazole is administered orally at a total daily dose of 200-800 mg twice a day. More optionally, the oral doses of Itraconazole is provided for a minimum of 14 days and a maximum of six months. It will be appreciated that a classical formulation of itraconazole or a super-bioavailability formulation will be administered. In general, the dose of the super-bioavailability will be 50% of the classical formulation.

DESCRIPTION OF DRAWINGS

Figure 1B:
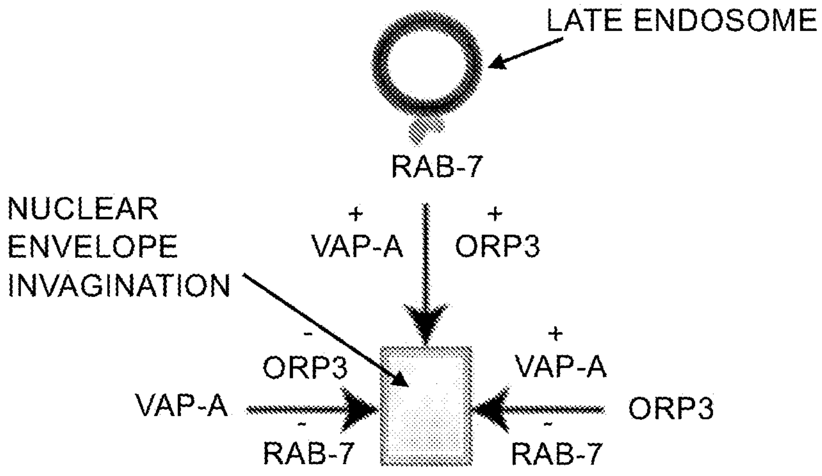
Figure 1C:
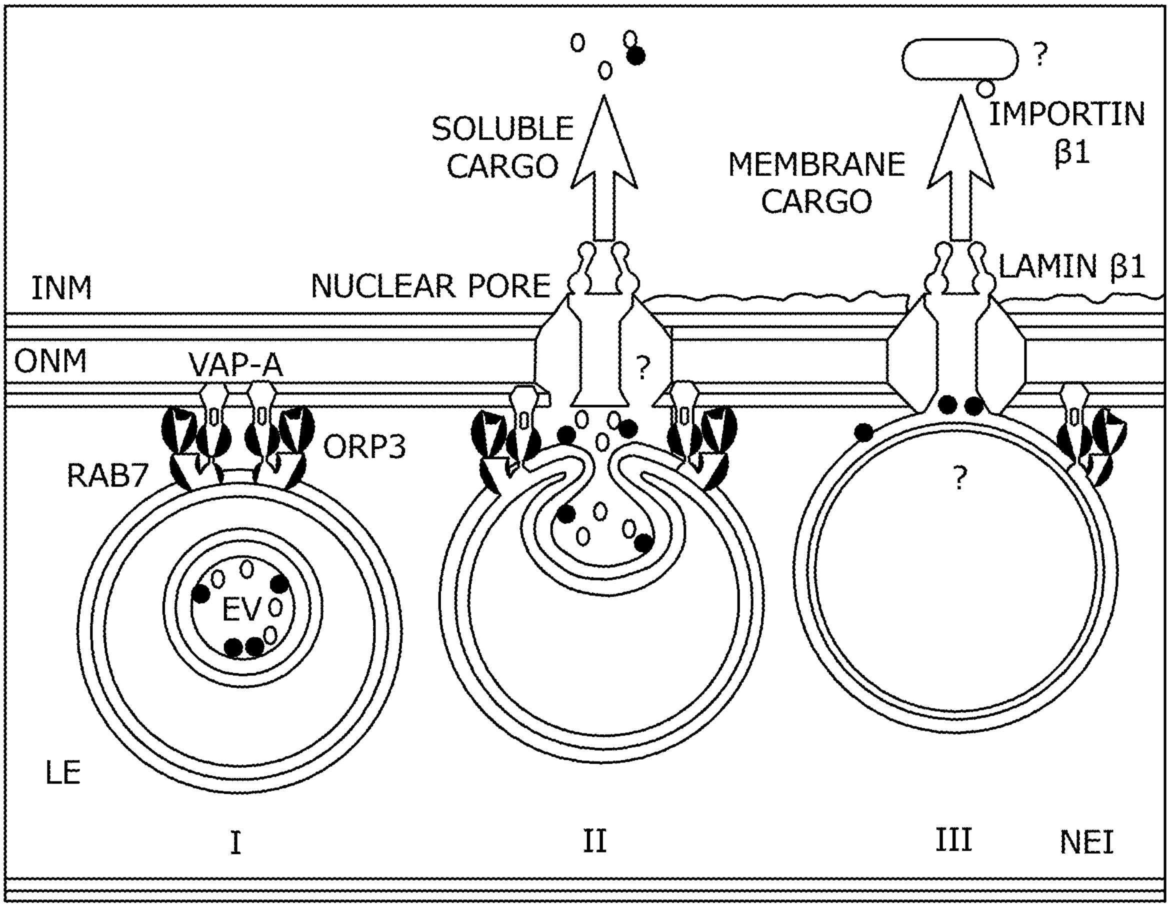

Referring to FIGS. 1A, 1B and 1C, illustrated are schematic illustrations of data showing the localization and the tripartite structure of a VOR complex. Notably, the VOR complex is localized in the nuclear envelope invagination. Typically, EVs are transported to late endosomes after their endocytosis, wherein the EVs facilitate intercellular communication in diverse cellular processes. Furthermore, the lack of the nuclear envelope invagination (NEI)-associated late endosomes and the inhibition of transfer of EV-derived components into the nucleoplasm of host cells after importazole treatment depicts the role of nuclear pores and importin β1 in the processes. Moreover, the potential interaction between the VOR complex and/or the NEI-associated late endosomes may significantly assist the processes. Notably, such processes allow the extraction of EV-derived membrane proteins from endosomal membrane and the subsequent transfer of the EV-derived membrane proteins into nucleoplasm through the nuclear pores of the host cells.

Referring to FIG. 1A, illustrated is a schematic illustration of type I and type II nuclear envelope invagination (NEI). VOR complex is associated with type II NEI.

Referring to FIG. 1B, illustrated is a schematic illustration of Rab7+ late endosomes in NEI. Typically, the presence of Rab7+ late endosomes in NEI requires VAP-A and ORP3. Furthermore, the presence of ORP3 is aided by VAP-A. In other words, the protein VAP-A and ORP3 co-exist mutually. Moreover, the protein VAP-A is associated with ONM of type II nuclear envelope invagination (NEI).

Referring to FIG. 1C, illustrated is a schematic illustration of the VOR complex proteins. Notably, the VOR complex contains the proteins such as VAP-A, ORP3, Rab7 and so forth. Typically, the VOR complex allows the tether of late endosomes to ONM in NEI of type II.

Figure 2:
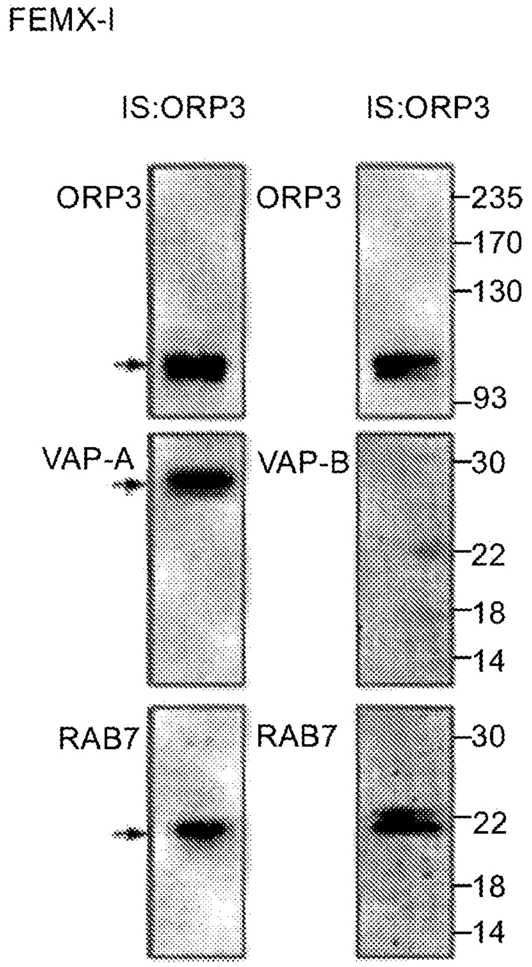
FIG. 2 is a schematic illustration of interaction between VAP-A, ORP3 and Rab7.

Referring to FIG. 2, illustrated is a schematic illustration of interaction between VAP-A, ORP3 and Rab7 in a nuclear envelope invagination. Typically, the detergent lysates prepared from FEMX-I cells are subjected to immunoisolation (IS) with anti-ORP3 antibody. Furthermore, the process of interaction is assisted by Protein G-coupled magnetic beads. Furthermore, entire bound fractions are probed for ORP3, VAP-A or VAP-B, and Rab7 by immunoblotting. As shown, the molecular mass markers (kDa) are indicated for each of the interaction. Notably, the arrows indicate the protein of interest and the consequent representative blots are depicted. It will be appreciated that no VAP-B is co-immunoisolated with ORP3 in contrast to VAP-A.

Referring to FIGS. 3A, 3B, 3C, 3D and 3E, illustrated are graphical representation of data depicting significance of tripartite complex for the nuclear transfer of EV-derived components.

Figure 3A:
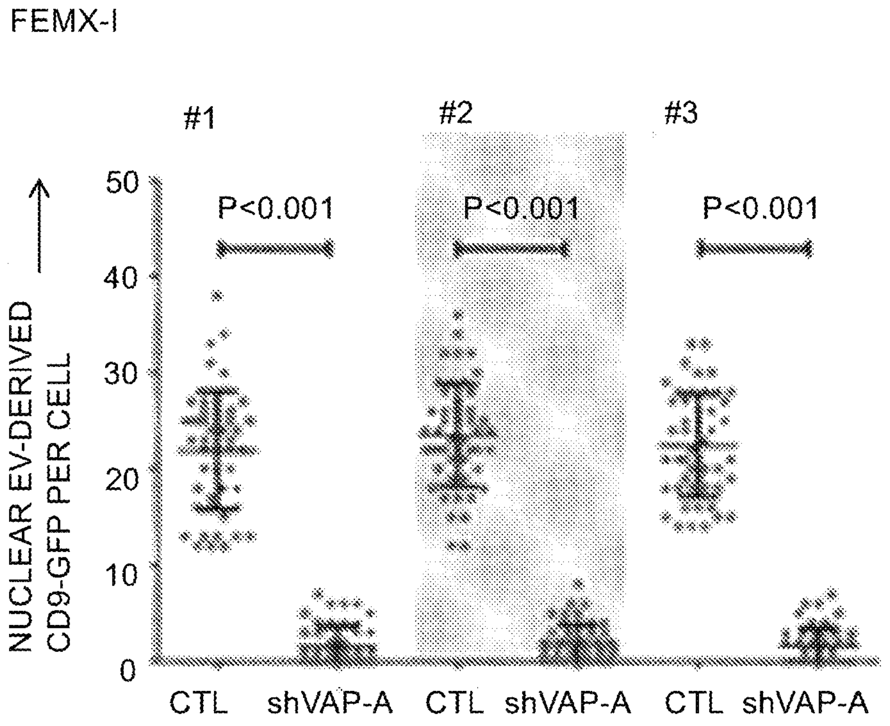
FIGS. 3A, 3B, 3C, 3D and 3E are graphical representation of data depicting significance of tripartite complex for the nuclear transfer of EV-derived components.

Referring to FIG. 3A, illustrated is a graphical representation of data associated with the nuclear EV-derived CD9-GFP. The fluorescent EVs derived from CD9-GFP-expressing FEMX-I cells are incubated with scrambled shRNA (control, Ctl) and shVAP-A, wherein the scrambled shRNA and shVAP-A are transfected FEMX-I cells. Furthermore, the cells are double-immunolabeled for VAP-A and SUN2 prior to confocal laser scanning microscopy (CLSM). Moreover, the amount of EV-derived CD9-GFP in the nuclear compartment is quantified to obtain data using processing tools such as Fiji. Typically, independent values for each cell from three independent experiments (#1-3) is depicted in the graphical representation. Moreover, more than 50 cells are evaluated to obtain the data associated therewith.

Figure 3B:
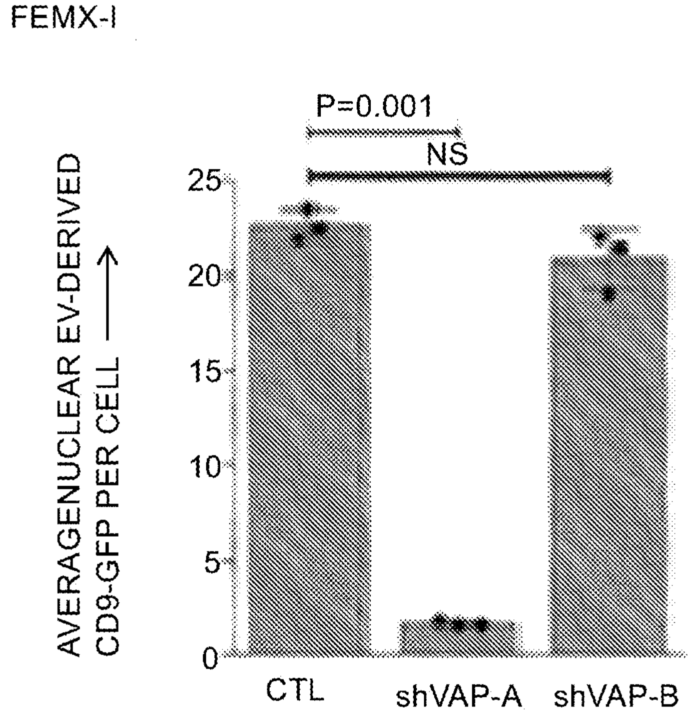

Referring to FIG. 3B, illustrated is a graphical representation of data associated with the average nuclear EV-derived CD9-GFP cell. The fluorescent EVs derived from CD9-GFP-expressing FEMX-I cells are incubated with scrambled shRNA (control, Ctl), shVAP-A and shVAP-B, wherein the scrambled shRNA, shVAP-A and the shVAP-B are transfected FEMX-I cells. Furthermore, the cells are double-immunolabeled for VAP-A or VAP-B and SUN2 prior to CLSM. Moreover, the amount of EV-derived CD9-GFP in the nuclear compartment is quantified to obtain data using processing tools such as Fiji. Typically, a mathematical average from the three independent experiments is depicted in the graphical representation. Moreover, more than 50 cells are evaluated to obtain the data associated therewith.

Figure 3C:
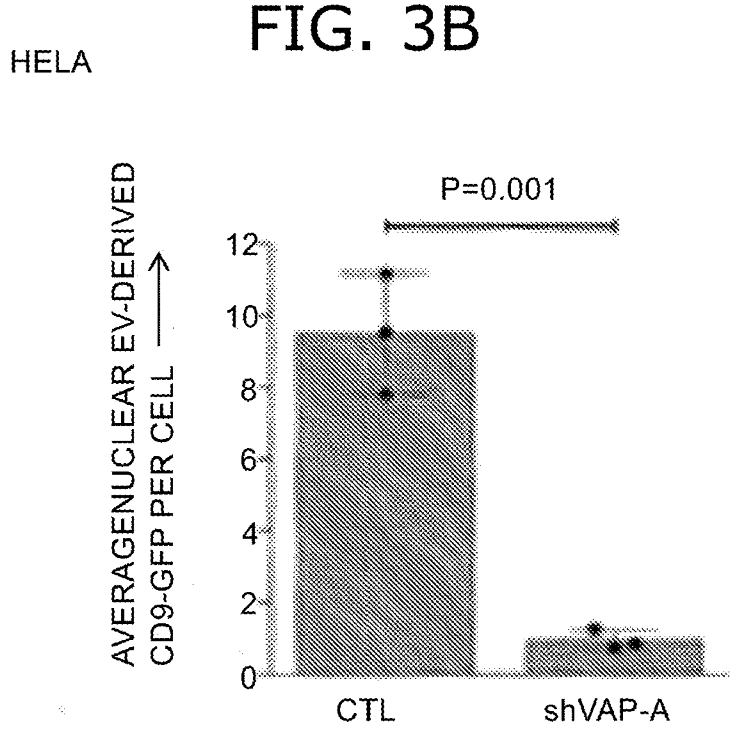

Referring to FIG. 3C, illustrated is a graphical representation of data associated with average nuclear EV-derived CD9-GFP per cell. The fluorescent EVs derived from CD9-GFP-expressing FEMX-I cells are incubated with scrambled shRNA (control, Ctl) and shVAP-A, wherein the scrambled shRNA and shVAP-A are transfected HeLa cells. Furthermore, the cells are double-immunolabeled for VAP-A and SUN2 prior to CLSM. Moreover, the amount of EV-derived CD9-GFP in the nuclear compartment is quantified to obtain data using processing tools such as Fiji. Typically, a mathematical average from the three independent experiments is depicted in the graphical representation. Moreover, more than 30 cells are evaluated to obtain the data associated therewith.

Figure 3D:
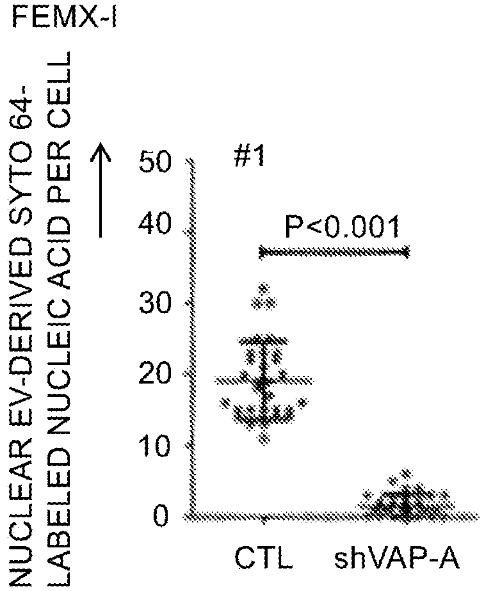
Figure 3E:
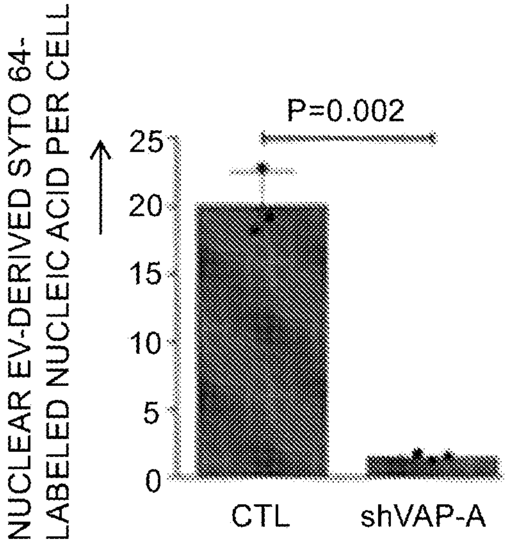

Referring to FIGS. 3D and 3E, illustrated is a graphical representation of data associated with nuclear EV-derived SYTO 64-Labeled Nucleic acid. Typically, scrambled shRNA (control, Ctl) or shVAP-A are incubated with SYTO 64-labeled EVs and further immunolabeled. Specifically, the scrambled shRNA and shVAP-A are transfected FEMX-I cells. Furthermore, nuclear SYTO 64 signals in a given cell (D) and an average from the three independent experiments (E) are quantified. Moreover, more than 30 cells are evaluated to obtain the data associated therewith.

Figure 4A:
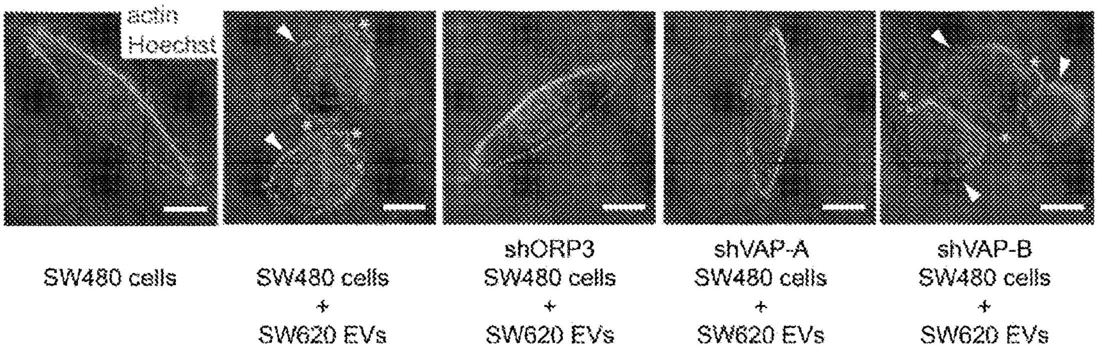
FIGS. 4A, 4B, 4C, are fluorescence microscopy illustration (A) and graphical representation (B, C) of data depicting the functional impact of tripartite complex on morphological alterations of SW480 cells mediated by EVs from SW620 cells.

Referring to FIG. 4A, illustrated is a CLSM (confocal laser-scanning microscopy) micrograph of SW480 cells, control and knockdown for specific proteins such as ORP3, VAP-A, or VAP-B, and treated with EVs derived from SW620 cells. Actin was immunolabeled with anti-actin antibody followed by a secondary antibody coupled to a fluorescent marker (FITC). The nucleus was stained with DAPI dye. Arrows point to rounded cells, while asterisks indicate evidence of blebbing. Scale bars, 10 μm.

Figure 4B:
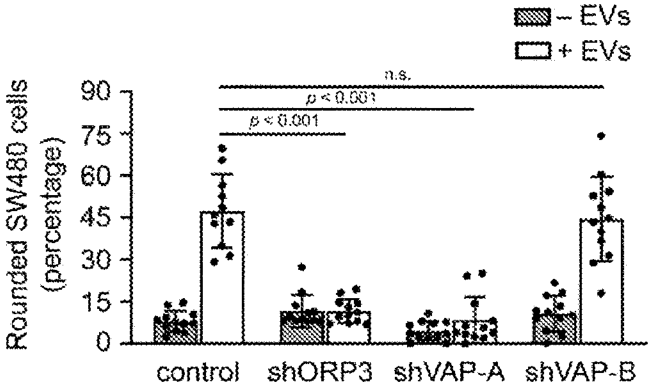
Figure 4C:
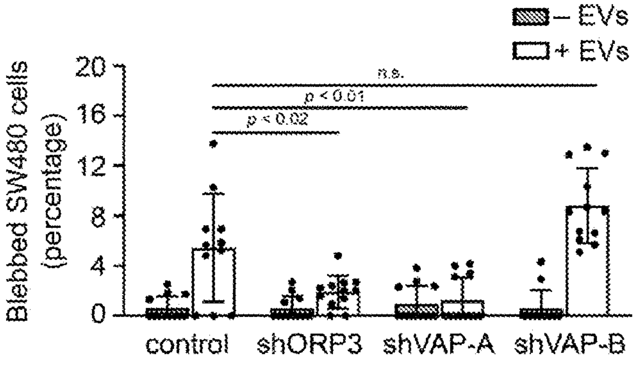

Referring to FIGS. 4B and 4C, illustrated is a graphical representation of data depicting the percentage of cells that have rounded (B) or blebbed (C) when exposed to EVs derived from SW620 cells for 5 hours. Cell morphology was analyzed after fixation.

Figure 5A:
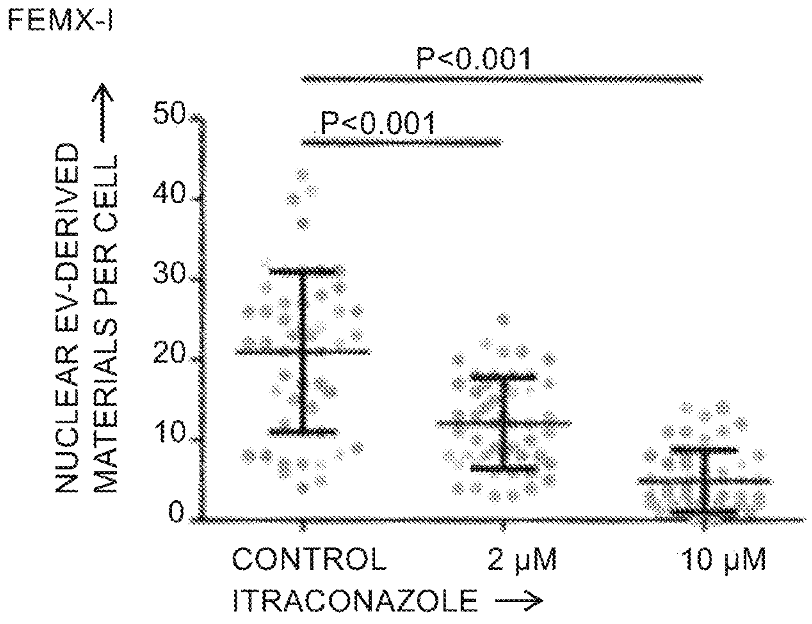
FIGS. 5A and 5B are graphical representation of data depicting the effect on inhibition of the VOR complex with respect to the EV-mediated intercellular communication.
Figure 5B:
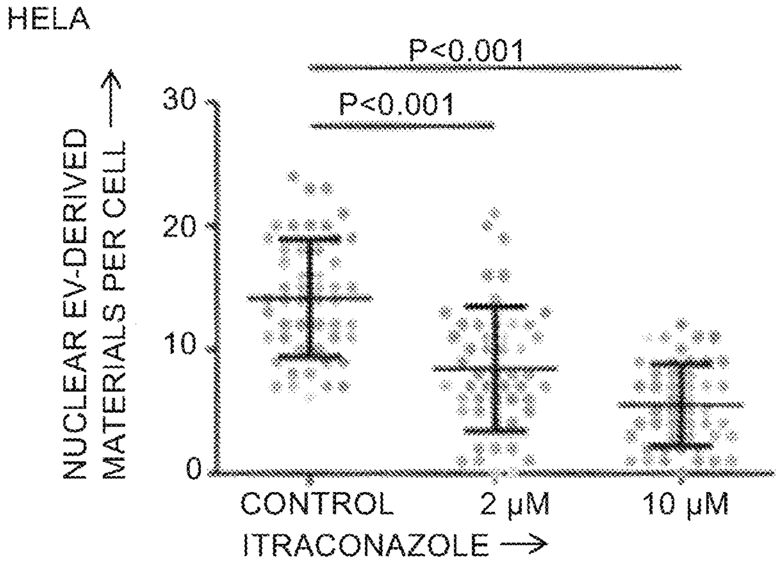

Referring to FIGS. 5A and 5B, illustrated is a graphical representation of data depicting the effect on inhibition of the VOR complex on FEMX-I cells (A) and Hela cells (B) with respect to the EV-mediated intercellular communication. Typically, the inhibition of VOR complex by itraconazole interferes with the nuclear transfer of the CD9-GFP$^+$ EV-derived cargo proteins.

Figure 6A:
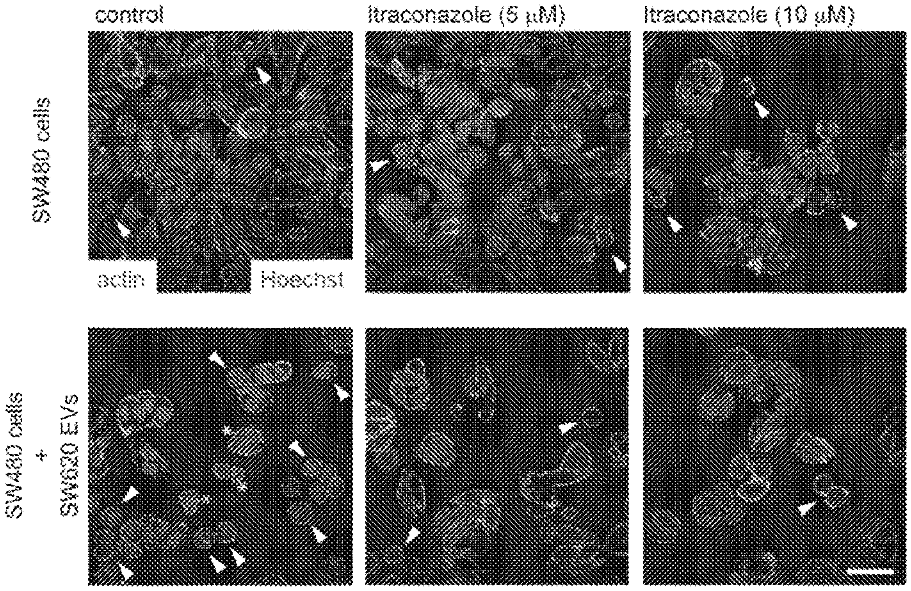
FIGS. 6A, 6B and 6C are fluorescence microscopy illustration (A) and graphical representation (B, C) of data depicting the effect on inhibition of the VOR complex with respect to the EV-mediated intercellular communication (ICZ, itraconazole; H-ICZ, hydroxy-itraconazole)
Figure 6B:
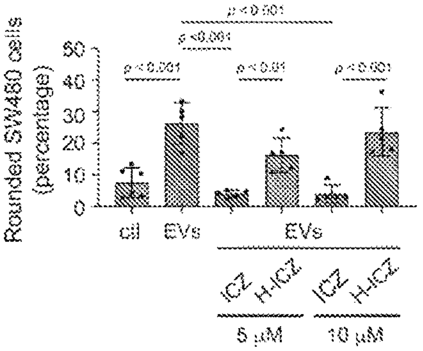
Figure 6C:
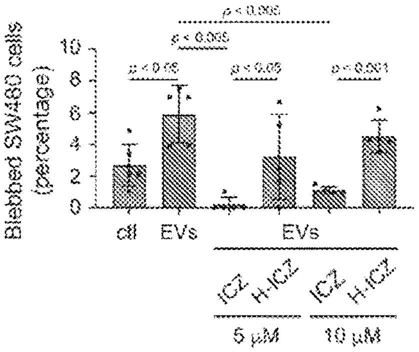

Referring to FIGS. 6A, 6B and 6C, illustrated is SW480 cells treated with 5 or 10 μM itraconazole (ICZ) or hydroxy-itraconazole (H-ICZ) for 10 min prior to incubation without or with EVs ($1\times10^9$) derived from SW620 cells for 5 hours. Micrograph of SW480 cells (A) stained with ActinGreen™ 488 ReadyProbes and counter-stained with DAPI. Arrows indicate rounded cells. Scale bar, 20 μm. The mean percent±standard deviation of rounded (B) and blebbed (C) cells treated with ICZ and H-ICZ with EVs. At least 50 cells were evaluated per independent experiment (n=6) per condition.

Figure 7A:
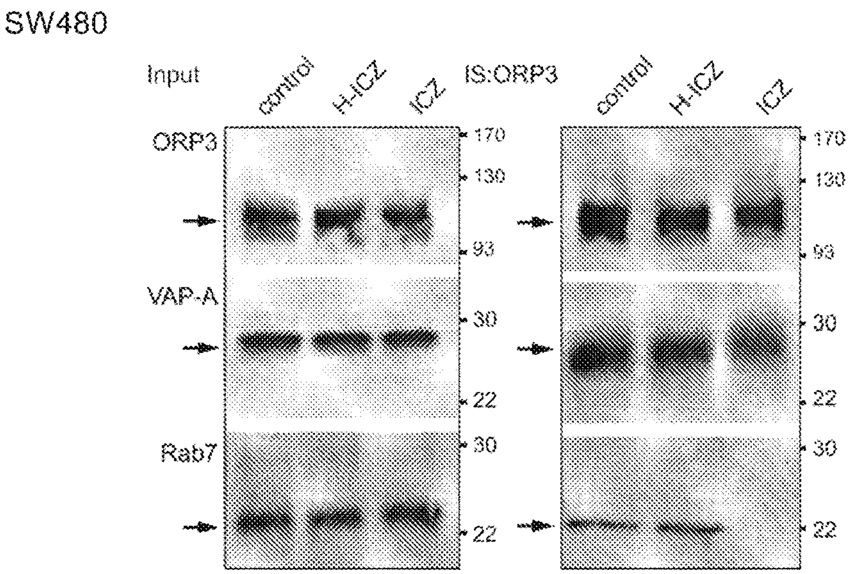
FIGS. 7A, 7B and 7C are schematic illustration (A) and graphical representation (B, C) of data showing the inhibition of the interaction between VAP-A, ORP3 and Rab7 (ICZ, itraconazole; H-ICZ, hydroxy-itraconazole)
Figure 7B:
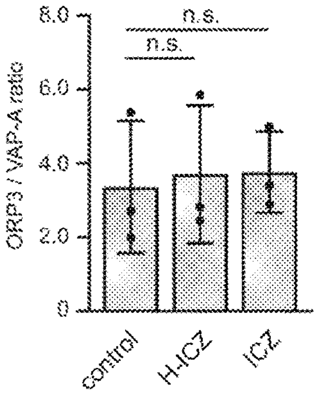
Figure 7C:
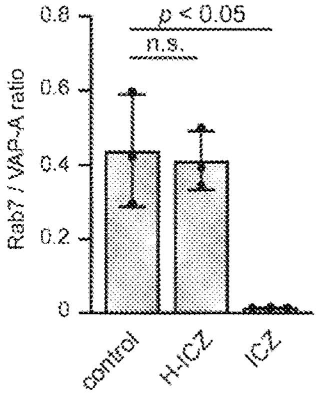

Referring to FIGS. 7A, 7B and 7C, illustrated is detergent lysates prepared from untreated (control) and 10 μM hydroxy-itraconazole—(H-ICZ) or itraconazole (ICZ)-treated SW480 cells were subjected to immunoisolation (IS) (right) with anti-ORP3 antibody followed by Protein G-coupled magnetic beads. The input used for IS is provided (left). Entire bound fractions were probed for ORP3, VAP-A, and Rab7 by immunoblotting. Note that no Rab7 is co-immunoisolated with ORP3 upon itraconazole treatment. The ratio of protein immunoreactivities of the indicated pairs, ORP3/VAP-A (B) and Rab7/VAP-A (C), was quantified (n=3). The mean±standard deviation are shown. N.s., not significant.

Figure 8A:
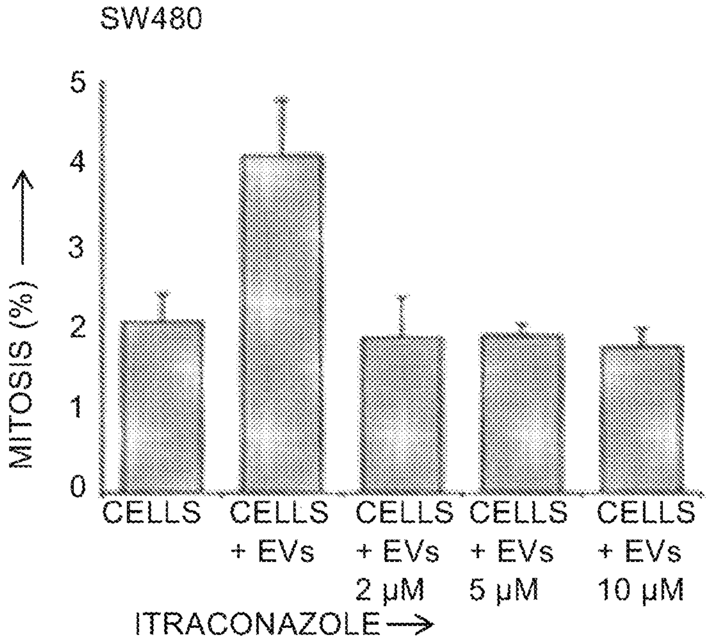
FIGS. 8A, 8B and 8C are graphical representation of data that depicts the therapeutic effect of inhibition of EV-mediated intercellular communication.

Referring to FIG. 8A, illustrated is a graphical representation of data associated with the treatment of SW480 cells with agent itraconazole. Specifically, the SW480 cells are treated with the agent itraconazole at concentrations of 0 (control), 2, 5 or 10 μM for 10 minutes. Furthermore, the SW480 cells are incubated with SW620 cell-derived EVs. Moreover, the incubated cells are stained with DAPI. Subsequently, the number of cell mitosis is scored and the cells are evaluated to obtain corresponding data. Notably, 500 cells are evaluated for a plurality of conditions.

Figure 8B:
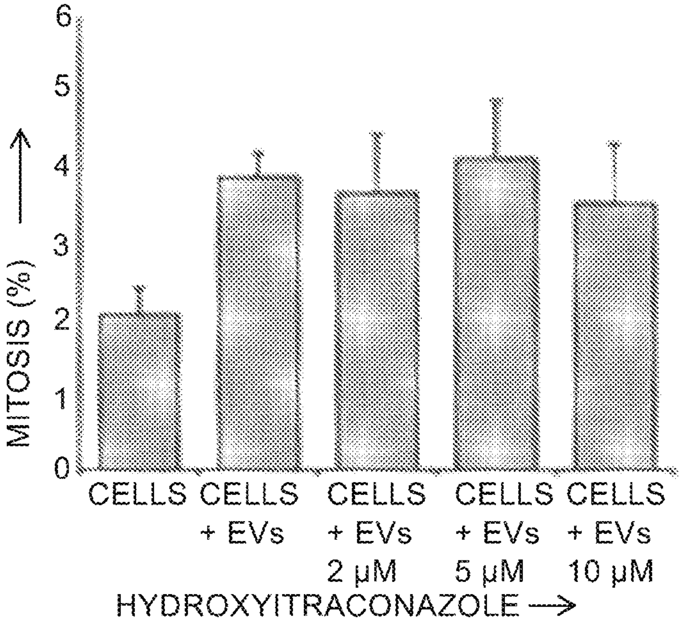

Referring to FIG. 8B, illustrated is a graphical representation of data associated with the treatment of SW480 cells with agent hydroxy-itraconazole. Specifically, the SW480 cells are treated with the agent hydroxy-itraconazole at concentrations of 0 (control), 2, 5 or 10 μM for 10 minutes. Furthermore, the SW480 cells are incubated with SW680 cell-derived EVs. Moreover, the incubated cells are stained with DAPI. Subsequently, the number of cell mitosis is scored and the cells are evaluated to obtain corresponding data. Notably, 500 cells are evaluated for a plurality of conditions.

Figure 8C:
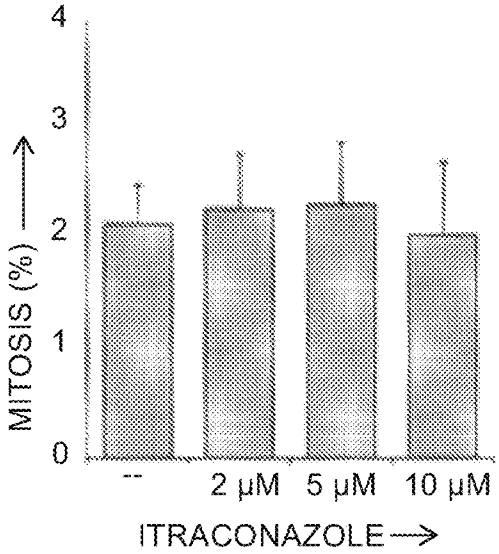

Referring to FIG. 8C, illustrated is a graphical representation of data associated with the treatment of SW480 cells with agent itraconazole. Specifically, the SW480 cells are treated with the agent itraconazole at concentrations of 0 (control, –) 2, 5 or 10 μM for 10 minutes. Furthermore, the SW480 cells are incubated for additional five hours. Moreover, the incubated cells are stained with DAPI. Subsequently, the number of cell mitosis is scored and the cells are evaluated to obtain corresponding data. Notably, 500 cells are evaluated for a plurality of conditions.

Figure 9:
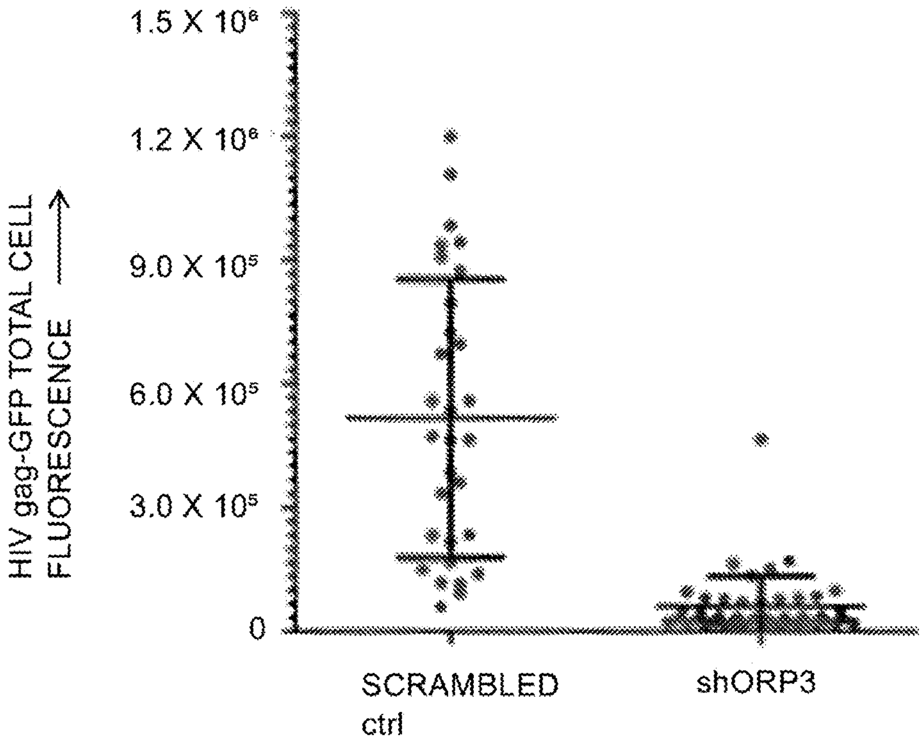
FIG. 9 is a graphical representation of data associated with the involvement of VOR complex with infectious cells.

Referring to FIG. 9, illustrated is a graphical representation of data associated with the involvement of VOR complex with infected cells. Specifically, the infected cells affected by HIV are employed. More specifically, transfected scrambled shRNA (control, Ctrl) and shORP3 FEMX-I cells are infected with HIVgag-GFP for twenty-four hours. Furthermore, mathematical tools such as region of interest (ROI) are employed to obtain the samples of interest. Consequently, the GFP fluorescence per cell is measured using processing tools such as Fiji.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method of inhibiting at least one member of a tripartite VAP-A, ORP3 and Rab7 (VOR) protein complex in multicellular organisms, for use in therapeutic intervention, wherein the method comprises:

selecting a compound for targeting the VOR protein complex, such that the inhibition causing interference with at least one mechanism of:

(a) intercellular communication, wherein the intercellular communication is mediated by receptor-ligand interaction and/or EVs; or (b) viral infection involving the transport of endocytosed biomaterials to the nucleus of recipient cells, the method further comprising mixing the chemical compound with the tripartite VAP-A, ORP3 and Rab7 (VOR) protein complex, wherein the chemical compound is Itraconazole or Itraconazole salt thereof or an Itraconazole analogue or Itraconazole analogue salts thereof.

2. A method according to claim 1, wherein inhibition of the tripartite VOR protein complex is a suppression of at least one member of the tripartite VAP-A, ORP3 and Rab7 (VOR) protein complex.

3. A method according to claim 1, wherein inhibition of the tripartite VOR protein complex is a suppression of the interaction between VAP-A and ORP3, ORP3 and Rab7, Rab7 and VAP-A, VAP-A and any member of the OSBP family, and/or any member of the OSBP family and Rab7.

4. A method according to claim 1, wherein the tripartite VOR protein complex is inhibited using a tripartite VOR protein complex inhibitor agent.

5. A method according to claim 3, wherein the compound is selected such that the binding of VAP-A to ORP3 is silenced.

* * * * *